United States Patent [19]

Suzuki

[11] Patent Number: 6,028,622
[45] Date of Patent: Feb. 22, 2000

[54] OBSERVATION APPARATUS FOR ENDOSCOPES

[75] Inventor: Takayuki Suzuki, Hachioji, Japan

[73] Assignee: Olympus Optical Co., Ltd., Tokyo, Japan

[21] Appl. No.: 09/064,840

[22] Filed: Apr. 23, 1998

[30] Foreign Application Priority Data

Apr. 25, 1997 [JP] Japan ................................. 9-109668

[51] Int. Cl.[7] ...................................................... A62B 1/04
[52] U.S. Cl. ............................................. 348/65; 600/160
[58] Field of Search ............................... 348/65, 68, 33, 348/164, 70; 600/109, 167, 181, 429, 476, 160, 178, 478, 477; 356/346; 250/461.2; 435/6; H04N 7/18

[56] References Cited

U.S. PATENT DOCUMENTS

| | | | |
|---|---|---|---|
| Re. 34,411 | 10/1993 | Nishioka et al. | 348/70 |
| 4,807,026 | 2/1989 | Nishioka et al. | 348/70 |
| 5,421,337 | 6/1995 | Richards-Kortum et al. | 600/477 |
| 5,749,830 | 5/1998 | Kaneko et al. | 600/160 |
| 5,784,162 | 7/1998 | Cabib et al. | 356/346 |

FOREIGN PATENT DOCUMENTS

| | | |
|---|---|---|
| 08224210 | 9/1996 | Japan . |
| WO 97/11636 | 4/1997 | WIPO . |

*Primary Examiner*—Bryan Tung
*Assistant Examiner*—Gims Philippe
*Attorney, Agent, or Firm*—Pillsbury Madison & Sutro LLP

[57] ABSTRACT

An observation apparatus for endoscopes includes a light source for illumination and an endoscope which has an illumination optical system for irradiating an object with light from the light source and an image-forming optical system for obtaining an image of the object illuminated through the illumination optical system, to observe the image with fluorescent light emanating from the object. This apparatus is provided with an excitation filter device placed in an optical path to irradiate the object with the light from the light source and an observation filter device disposed in an optical path to obtain the image of the object. The excitation filter device includes a first filter having spectral transmittances such as to have a cutoff wavelength region on the short-wavelength side of wavelengths of the fluorescent light and to transmit light with shorter wavelengths than in the cutoff wavelength region. On the other hand, the observation filter device includes a fluorescence observation filter having spectral transmittances such as to have a cutoff wavelength region on the short-wavelength side of wavelengths of the fluorescent light and to transmit light with longer wavelengths than in this cutoff wavelength region. In this way, the transmissive wavelength regions of the first filter and the fluorescence observation filter are superposed at any wavelength in a wavelength region of at least 440–460 nm.

7 Claims, 3 Drawing Sheets

OBSERVATION APPARATUS FOR ENDOSCOPES

BACKGROUND OF THE INVENTION

1. Field of the Invention

This invention relates to an observation apparatus for endoscopes which is suitable for observations on a tumor and the like in a human body, and in particular to an observation system for endoscopes including this apparatus.

2. Description of Related Art

The observation of a tumor requires the use of a particular drug which has properties of being easy to gather on a cancerous cell and of emitting fluorescent light by the irradiation of light. Specifically, the drug with such properties is made to penetrate an object to be observed by means of injection or spraying, and the object is irradiated with excitation light through an excitation filter which transmits components lying in a region of relatively short wavelengths, of light from a light source, so that fluorescent light emanates from a particular part of the object. This fluorescent light is introduced into a TV camera, through an observation filter which blocks the excitation light to transmit components in a region of relatively long wavelengths including fluorescence wavelengths, so that a fluorescent image is obtained.

In a conventional system of this type, the transmissive wavelength region of the excitation filter is independent of that of the observation filter and thus the fluorescent image is observed against a dark background. This situation obscures the relative relationship between the image of the object as seen with the unaided eye and the fluorescent image. Hence, a technique has been used that the image of the object is formed with visible light by using proper means, and this image (ordinary image) and the fluorescent image are displayed in parallel on a single TV monitor. The result is that the images are very hard to see in practice and this fact becomes a great burden to an observer.

SUMMARY OF THE INVENTION

It is, therefore, an object of the present invention to provide an observation apparatus for endoscopes and in particular an observation system for endoscopes including this apparatus in which the ordinary image and the fluorescent image can be seen with them superposed and an arrangement is simple.

In order to achieve this object, the observation apparatus for endoscopes according to the present invention includes a light source for illumination and an endoscope which has an illumination optical system for irradiating an object to be observed with light from the light source and an image-forming optical system for bringing about an image of the object illuminated through the illumination optical system, to observe the image with fluorescent light emanating from the object. The observation apparatus for endoscopes is provided with an excitation filter means placed in an optical path to irradiate the object with the light from the light source and an observation filter means disposed in an optical path to bring about the image of the object. The excitation filter means includes a first filter having spectral transmittances such as to have a cutoff wavelength region on the short-wavelength side of wavelengths of the fluorescent light and to transmit light with shorter wavelengths than in the cutoff wavelength region. On the other hand, the observation filter means includes a fluorescence observation filter having spectral transmittances such as to have a cutoff wavelength region on the short-wavelength side of wavelengths of the fluorescent light and to transmit light with longer wavelengths than in this cutoff wavelength region. In this way, the transmissive wavelength regions of the first filter and the fluorescence observation filter are superposed at any wavelength in a wavelength region of at least 440–460 nm.

According to the present invention, the excitation filter means includes a second filter having cutoff wavelength regions on the short-wavelength side of the wavelengths of the fluorescent light, and is placed so that the first and second filters can be selectively introduced into, or removed from, the optical path.

Further, according to the present invention, when an average value of spectral transmittances at wavelengths $\lambda$ in a wavelength region of 350–700 nm is denoted by $TL(\lambda)$, the first and second filters are designed so that respective values of $TL(\lambda)$ of the first filter are defined by Eq. (1) shown below and those of $TL(\lambda)$ of the second filter are defined by Eq. (2). In this case, it is assumed that the amount of light of wavelengths incident on each of the first and second filters is 100%.

$$\left. \begin{array}{l} \text{When } \lambda = 350\text{–}420 \text{ nm, } T_{L(350\text{–}420)} \geq 60\% \\ \text{When } \lambda = 440\text{–}460 \text{ nm, } 24\% \leq T_{L(440\text{–}460)} \leq 35\% \\ \text{When } \lambda = 460\text{–}700 \text{ nm, } T_{L(460\text{–}700)} < 0.7\% \end{array} \right\} \quad (1)$$

$$\left. \begin{array}{l} \text{When } \lambda = 350\text{–}420 \text{ nm, } T_{L(350\text{–}420)} \geq 60\% \\ \text{When } \lambda = 440\text{–}460 \text{ nm, } 8\% \leq T_{L(440\text{–}460)} \leq 23\% \\ \text{When } \lambda = 460\text{–}700 \text{ nm, } T_{L(460\text{–}700)} < 0.7\% \end{array} \right\} \quad (2)$$

The observation system for endoscopes according to the present invention is such that the object is irradiated with excitation light including blue components in the visible wavelength region and components with shorter wavelengths than the blue components, through the illumination optical system of the endoscope; fluorescent light emanating from the object, with longer wavelengths than the excitation light and part of the blue components of the excitation light reflected from the object are imaged at the same time through the image-forming optical system of the endoscope; and an image of the object of a bluish hue caused by the blue components of the excitation light and an image of the object by the fluorescent light are superposed and displayed on a monitor means. Here, it is desirable that the blue components contain any wavelength in a wavelength region of at least 440–460 nm.

Further, the observation system for endoscopes according to the present invention is designed to allow the changeover of a first mode for recognizing the position of production of the fluorescent light in an object to be observed in such a way that the object is irradiated with first excitation light including blue components in the visible wavelength region and components with shorter wavelengths than the blue components through the illumination optical system of the endoscope; first fluorescent light emanating from the object, with longer wavelengths than the first excitation light, and the blue components of the first excitation light reflected from the object are imaged simultaneously through the image-forming optical system of the endoscope; and an image of the object of a bluish hue caused by the blue components of the first excitation light and an image of the object by the first fluorescent light are superposed and displayed on a monitor means, and a second mode for mainly observing a fluorescent image in such a way that the object is irradiated with second excitation light lower in intensity of the blue components in the visible wavelength region than the first excitation light; second fluorescent light emanating from the object, with longer wavelengths than the second excitation light, and blue components of the second excitation light reflected from the object are imaged simultaneously through the image-forming optical system of the endoscope; and an image of the object of a thinner bluish hue than in the first mode, caused by the blue components of the second excitation light and an image of the object by the second fluorescent light are superposed and displayed on the monitor means. Here, it is desirable that the blue components contain any wavelength in a wavelength region of at least 440–460 nm. In this case, a comparison of intensities of the blue components between the first excitation light and the second excitation light is made in accordance with the extent of wavelengths of light contained in these wavelength regions.

The observation apparatus for endoscopes according to the present invention is provided with a light source in which two kinds of light including components with wavelengths of light ranging from an ultraviolet to a blue region and white light are selectively emitted; a light guide cable receiving the light from the light source to introduce it into an rigid endoscope; a fluorescence observation filter placed In an observation optical system of the rigid endoscope; a TV camera device for displaying an observation image formed by the rigid endoscope on a monitor; and a changeover switch, preferably constructed with a foot control switch, for selecting the kind of light emitted from the light source.

Further, the observation apparatus for endoscopes according to the present invention is designed so that when the average value $TL(\lambda)$ of spectral transmittances of the excitation filter means at wavelengths $\lambda$ in a wavelength region of 350–700 nm is multiplied by an average value $TS(\lambda)$ of spectral transmittances of the fluorescence observation filter, the multiplied average values are defined by the following conditions. In this case, it is assumed that the amount of light of wavelengths incident on each of the excitation filter means and the fluorescence observation filter is 100%.

$$\left. \begin{array}{l} \text{When } \lambda = 350\text{–}440 \text{ nm}, \; T_{L(350-440)} \times T_{S(350-440)} \leq 0.3\% \\ \text{When } \lambda = 440\text{–}460 \text{ nm}, \; 0.5\% \leq T_{L(440-460)} \times T_{S(440-460)} \leq 10\% \\ \text{When } \lambda = 460\text{–}700 \text{ nm}, \; T_{L(460-700)} \times T_{S(460-700)} \leq 0.3\% \end{array} \right\} \quad (3)$$

This and other objects as well as the features and advantages of the present invention will become apparent from the following detailed description of the preferred embodiment when taken in conjunction with the accompanying drawings.

DETAILED DESCRIPTION OF THE PREFERRED EMBODIMENT

Figure 1:
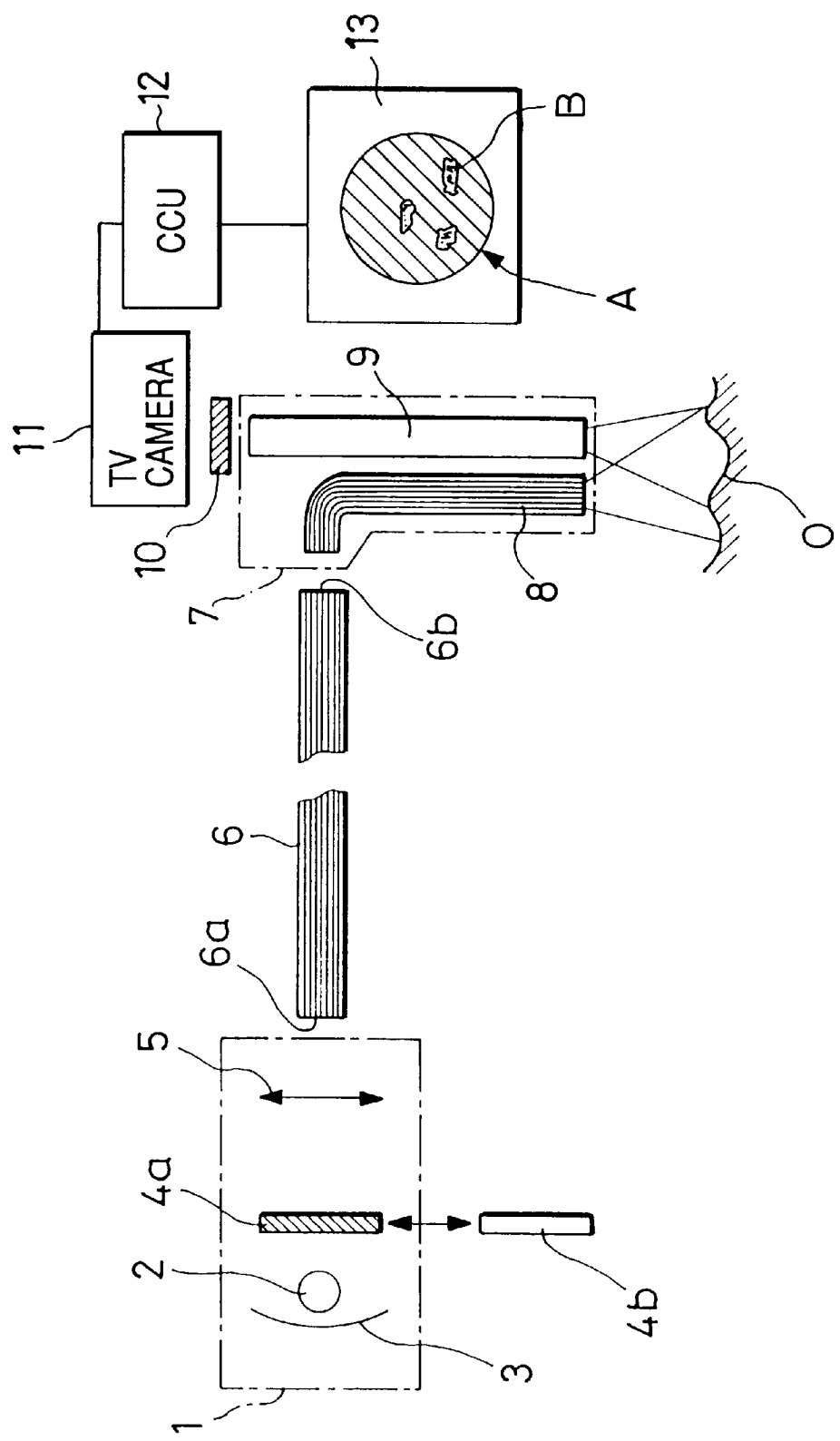
FIG. 1 is a schematic view showing an observation apparatus for endoscopes according to the present invention.

In accordance with the embodiment shown in the drawings, the present invention will be explained in detail below. In FIG. 1, reference numeral 1 represents a light source for illumination including a source lamp 2, such as a halogen lamp, xenon lamp, metal halide lamp, etc.; a concave mirror 3 for collecting light from the source lamp 2; two kinds of filters 4a and 4b, which will be described later, introduced to be switchable into a light beam produced by light from the concave mirror 3: and a condenser lens 5 for condensing the light beam transmitted through the filter 4a or 4b on an entrance end face 6a of a light guide fiber bundle 6 encased in a light guide cable. Also, between the source lamp 2 and the light guide cable, various filters, for example, an infrared cutoff filter and the like, are usually interposed to make a good observation.

Reference numeral 7 designates an endoscope including a light guide fiber bundle 8 for receiving the light beam emerging from an exit end face 6b of the light guide fiber bundle 6 on the entrance end side thereof to emit illumination light toward an object 0 to be observed and an observation optical system 9 for observing an image of the illuminated object 0. The endoscope 7, whose structure is too familiar to need a detailed explanation, is such that an illumination lens for changing a spread angle of the illumination light is placed at the tip of the light guide fiber bundle 8 when necessary. Where the endoscope 7 is constructed with a fiberscope, the observation optical system 9 has an objective lens, an image guide fiber bundle for transmitting the image of the object 0 formed by the objective lens, and an eyepiece for observing the image appearing on the exit end face of the image guide fiber bundle. On the other hand, where the endoscope 7 is a rigid endoscope, the observation optical system 9 is provided with a relay lens system instead of the image guide fiber bundle. Also, between the exit end face 6b of the light guide fiber bundle 6 and the entrance end face of the light guide fiber bundle 8, a connection optical system composed of lenses is interposed when necessary.

Reference numeral 10 denotes a filter, which will be described later, disposed outside the eyepiece section of the observation optical system 9; 11, a TV camera head placed outside the filter 10, incorporating an imaging lens, an image sensor (CCD), and an electric circuit with a minimum of configuration required; 12, a signal processing circuit (which is called a camera control unit, CCU, and incorporates various control circuits not only for simple TV signal processing, but also for more complicated image processing) for processing a TV signal delivered from the TV camera head; and 13, a TV monitor. The filter 10 may be placed in the observation optical system 9 or the TV camera head 11, and in this case, the TV camera head 11 is removably mounted to the endoscope 7.

Figure 2:
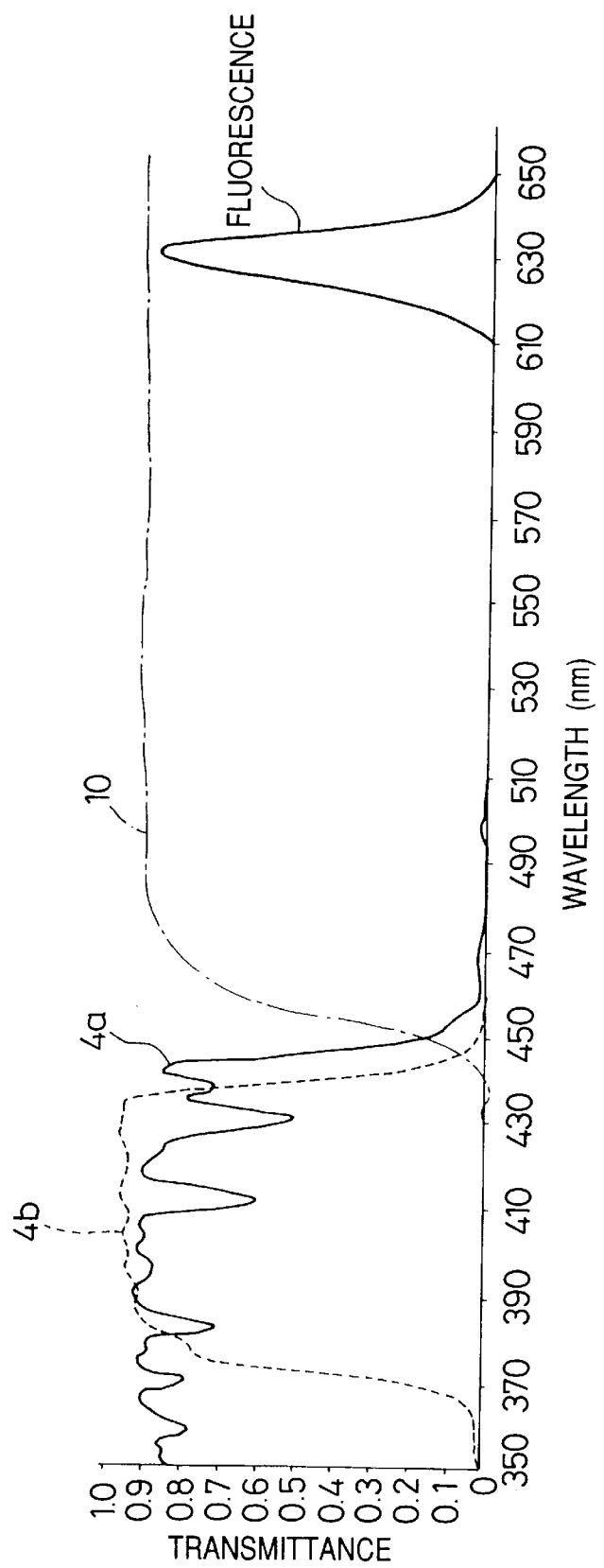
FIG. 2 is a diagram showing spectral transmittance characteristics of two kinds of filters used to be switchable in a light source of the observation apparatus for endoscopes shown in FIG. 1 and a filter used for observation and spectral characteristics of fluorescent light from an object to be observed.

The filter 4a, as shown in FIG. 2, has spectral transmittances such as to have a cutoff wavelength region, namely a wavelength region where the transmittance becomes zero, on the short-wavelength side of wavelengths (630±20 nm) of fluorescent light and to transmit light with shorter wavelengths than in the cutoff wavelength region. The filter 4b has spectral transmittances such as to have two cutoff wavelength regions on the short-wavelength side of wavelengths (630±20 nm) of fluorescent light and to transmit light of wavelengths between the two cutoff wavelength regions. In both the filters 4a and 4b, their spectral transmittance characteristics are selected so that the filters function as excitation filters for fluorescence observation. Also, although the filter 4b is designed so that the transmittance is nearly zero in the vicinity of wavelength 460 nm, the filter 4a is such that the position of the wavelength where the transmittance becomes zero is somewhat shifted to the long-wavelength side of the filer 4b. On the other hand, the filter 10 has spectral transmittances such as to have a cutoff wavelength region on the short-wavelength side of the wavelengths of the fluorescent light and to transmit yellow light (green+red) on the long-wavelength side of the cutoff wavelength region. The spectral transmittance characteristics of the filter 10 are selected so that the filter 10 serves as a fluorescence observation filter and a combined transmittance of the filter 10 with the filters 4a and 4b forms a crest with a peak in the vicinity of wavelength 450 nm. Also, the area of overlapping of the transmissive wavelength regions of the filter 4b and the filter 10 is smaller than that of overlapping of the transmissive wavelength regions of the filter 4a and the filter 10. For the filter 10, it is favorable that, for example, absorption glass GG455 made by Schott is used by setting a proper thickness of glass so as to have the transmittance suitable for fluorescence observation.

Subsequently, for example, in a case where fluorescent drug ALA (5-aminolevulinic acid) is used for the fluorescence observation and treatment of an intravesical tumor, the use and function of the apparatus according to the present invention are explained.

First, the affected part which is regarded as the intravesical tumor is sprayed with the fluorescent drug ALA 2–3 hours before the start of the observation. When the observation is started, the filter 4a is inserted in the optical path between the source lamp 2 of the light source 1 for illumination and the condenser lens 5, and the affected part is irradiated with blue light as the excitation light, with wavelengths as a center at 409 nm. At this time, fluorescent light (red light) with wavelengths of 630±20 nm is produced from a place where the tumor exists, while illumination light is diffusedly reflected from a place where the tumor does not exist. The fluorescent light and the illumination light are both captured by the observation optical system 9. In this case, the filter 10 introduced into the observation system, because of its transmittance-wavelength characteristics shown in FIG. 2, transmits simultaneously the fluorescent light and the blue light which lies in a wavelength region of 440–460 nm. These two kinds of light form an image through the TV camera head 11, and the image is displayed through the signal processing circuit 12 on the TV monitor 13 so that, as shown in FIG. 1, affected parts B, namely tumor parts, look red (white in the figure) and bright against a background A of relatively bright blue (indicated by hatching in the figure). Consequently, an operator views the image on the TV monitor 13 and thereby can easily find the intravesical tumor parts.

Subsequently, the filter 4a placed in the light source 1 for illumination is replaced with the filter 4b for observation. In this case, since the amount of blue light of the background A on the TV monitor 13 is considerable small compared with the case of the filter 4a, the tumor parts can be clearly viewed in an extremely dark (but faintly visible) background. This facilitates the definition of the limit of the tumor, that is, the boundaries of the tumor parts. Subsequent treatment (removal of the tumor) is securely given in such a way that the filter 4b is replaced again with the filter 4a and the positional relationship between a treatment tool and the tumor or other parts is adequately maintained in the dark background. After the treatment, the filter 4a is further replaced with the filter 4b to make sure that the tumor has been completely removed. Even if the tumor still remains very small, it will appear to be red and bright, and thus it is only necessary to still further replace the filter 4b with the filter 4a for treatment. In this way, the operator can remove the tumor completely and easily while viewing the image on the TV monitor 13.

In this case, since the time during which a fluorescence reaction is produced in a single drug spraying is limited to 10–20 minutes, rapid observation and treatment are required. It is thus desirable that the changeover of the filters 4a and 4b is electrically performed by using a foot control switch placed close to the operator's feet or a changeover switch provided in an endoscope holding section.

Figure 3:
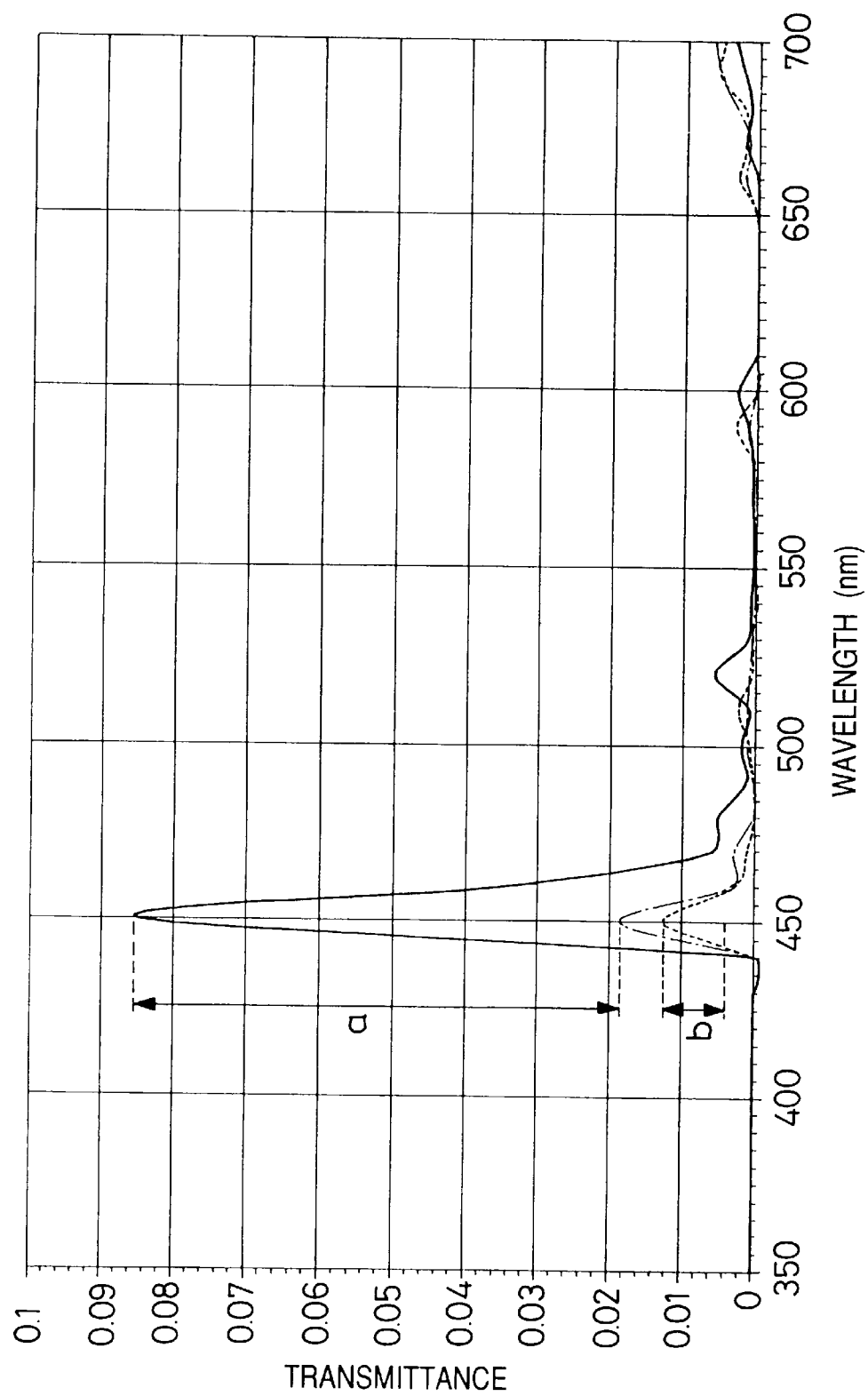
FIG. 3 is a transmittance characteristic diagram where spectral transmittance characteristic curves of two kinds of filters in the light source and the filter for observation are superposed.

FIG. 3 shows a transmittance characteristic diagram (corresponding to the characteristic diagram at wavelengths of 440–460 nm in FIG. 2) where the spectral transmittance characteristic curves of the filters 4a and 4b replaced with each other in the light source 1 overlap with that of the filter 10 to be incorporated in the observation optical system, representing the intensity of light of background color. In this characteristic diagram, it is experimentally verified that if the transmittance lies in a range a, background color (blue) and fluorescent color (red) will be seen with proper brightness; beyond the upper limit of the range a, the background color is so much heavy that the fluorescent color is hard to see; and below the lower limit, the background is extremely dark and its orientation becomes difficult.

On the other hand, if the transmittance lies in a range b, the background becomes dark and thus work such as orientation is difficult, but a sharper fluorescent image can be observed in a state that the background is faintly visible. This is effective in viewing the extent of spread of the affected part or in ascertaining whether the affected part, after being removed, still remains. If the transmittance exceeds the upper limit of the range b, the background becomes extremely bright and the fluorescent image becomes blurred. Below the lower limit of the range b, the background becomes pitch dark and thus the position of the affected part ceases to be confirmable.

As the above experimental results, when the amount of light of wavelengths incident on each of the filters 4a and 4b is assumed as 100% and an average value of spectral transmittances at the wavelengths $\lambda$ in a wavelength region of 350–700 nm is denoted by TL($\lambda$), it Is favorable that respective values of TL($\lambda$) of the filter 4a are defined by Eq. (1) already mentioned and those of TL($\lambda$) the filter 4b are defined by Eq. (2).

Furthermore, when the average value TL($\lambda$) of spectral transmittances of each of the filters 4a and 4b at the wavelengths $\lambda$ in a wavelength region of 350–700 nm is multiplied by the average value TS($\lambda$) of spectral transmittances of the filter 10, it is desirable that the multiplied average values are defined by Eq. (3). Here, it is assumed that the amount of light of wavelengths incident on each of the filters 4a and 4b and the filter 10 is 100%.

Although, in the above embodiment, reference has been made to the case where the intravesical tumor is observed and treated, it is needless to say that the present invention is not limited to this case and is applicable to observations and treatments of other organs.

What is claimed is:

1. An observation apparatus for endoscopes, comprising:
   an illumination light source;
   an endoscope having an illumination optical system constructed and arranged to irradiate an object to be observed with light from said illumination light source and an image-forming optical system constructed and arranged to obtain an image of the object illuminated through said illumination optical system and to observe the image with fluorescent light emanating from the object;
   an excitation filter system placed in an optical path of illumination light from said illumination light source; and
   an observation filter system disposed in an optical path of light that is formed into the image of the object, said excitation filter system including:
- a first filter having a spectral transmittances including a cutoff wavelength region on a short-wavelength side of wavelengths of the fluorescent light and a transmitting wavelength region at shorter wavelengths than in the cutoff wavelength region of said first filter, and
- a second filter with a cutoff wavelength region that is shifted from the cutoff wavelength region of said first filter toward a short-wavelength side,
- said first filter and said second filter being constructed and arranged to be selectively insertable in and out of the optical path of illumination light, said observation filter system including a fluorescence observation filter having a spectral transmittance including a cutoff wavelength region on a short-wavelength side of wavelengths of the fluorescent light and a transmitting wavelength region at longer wavelengths than in the cutoff wavelength region of said fluorescence observation filter, wherein transmissive wavelength regions of said first filter and said fluorescence observation filter are superposed at least at a wavelength in a wavelength region of 440–460 nm.

2. An observation apparatus for endoscopes according to claim 1, wherein when an average value of spectral transmittances at wavelengths $\lambda$ in a wavelength region of 350–700 nm is denoted by $T_{L(\lambda)}$, respective values of $T_{L(\lambda)}$ of said first filter are defined by the following conditions:

when $\lambda$=350–420 nm, $T_{L(350-420)} \geq 60\%$ when $\lambda$=440–460 nm, $24\% \leq T_{L(440-460)} \leq 35\%$ when $\lambda$=460–700 nm, $T_{L(460-700)} < 0.7\%$ and respective values of $T_{L(\lambda)}$ of said second filter are defined by the following conditions:

when $\lambda$=350–420 nm, $T_{L(350-420)} \geq 60\%$ when $\lambda$=440–460 nm, $8\% \leq T_{L(440-460)} \leq 23\%$ when $\lambda$=460–700 nm, $T_{L(460-700)} < 0.7\%$ where it is assumed that an amount of light of wavelengths incident on each of said first filter and said second filter is 100%.

3. An observation system for endoscopes which allows a changeover of:
- a first mode for recognizing the position of production of fluorescent light in an object to be observed wherein that the object is irradiated with first excitation light including blue components in a visible wavelength region and components with shorter wavelengths than the blue components through an illumination optical system of an endoscope; first fluorescent light emanating from the object, with longer wavelengths than said first excitation light and the blue components of said first excitation light reflected from the object are imaged simultaneously through an image-forming optical system of the endoscope; and an image of the object of a bluish hue caused by the blue components of said first excitation light and an image of the object by said first fluorescent light are superposed and displayed on monitor means, and
- a second mode for mainly observing a fluorescent image wherein that the object is irradiated with second excitation light lower in intensity of the blue components in the visible wavelength region than said first excitation light; second fluorescent light emanating from the object, with longer wavelengths than said second excitation light and blue components of said second excitation light reflected from the object are imaged simultaneously through the image-forming optical system of the endoscope; and an image of the object of a thinner bluish hue than in the first mode, caused by the blue components of said second excitation light and an image of the object by said second fluorescent light are superposed and displayed on the monitor means.

4. An observation apparatus for endoscopes according to claim 1, wherein when an average value $T_{L(\lambda)}$ of spectral transmittances of said excitation filter means at wavelengths $\lambda$ in a wavelength region of 350–700 nm is multiplied by an average value $T_{S(\lambda)}$ of spectral transmittances of said fluorescence observation filter, multiplied average values are defined by the following conditions:

when $\lambda$=350–440 nm, $T_{L(350-440)} \times T_{S(350-440)} \leq 0.3\%$ when $\lambda$=440–460 nm, $0.5\% \leq T_{L(440-460)} \times T_{S(440-460)} \leq 10\%$ when $\lambda$=460–700 nm, $T_{L(460-700)} \times T_{S(460-700)} \leq 0.3\%$ where it is assumed that the amount of light of wavelengths incident on each of said excitation filter means and said fluorescence observation filter is 100%.

5. A method of observing an object with an endoscope, comprising:
- illuminating an object with illumination light from a light source, said illumination light defining an illumination optical path that passes through at least a portion of an endoscope, wherein said illumination light causes said object to fluoresce;
- filtering said illumination light with an excitation filter, said excitation filter having a higher attenuation for wavelengths that are longer than a preselected excitation filter cutoff wavelength than for wavelengths that are shorter than said preselected excitation filter cutoff wavelength;
- filtering light emanating from said object with an observation filter, said observation filter having a lower attenuation for wavelengths that are longer than a preselected observation filter cutoff wavelength than for wavelengths that are shorter than said preselected observation filter cutoff wavelength, wherein said light emanating from said object is a combination of redirected illumination light and fluorescent light;
- collecting and imaging light subsequent to said filtering light emanating from said object using said endoscope, wherein said preselected observation cutoff wavelength is at a shorter wavelength value than said preselected excitation filter cutoff.

6. A method of observing an object with an endoscope according to claim 5, wherein said preselected excitation filter cutoff wavelength and said preselected excitation filter cutoff wavelength are in a region of the visible spectrum of light between the blue and violet regions of the visible spectrum.

7. A method of observing an object with an endoscope according to claim 5, wherein said excitation filter is replaced with another excitation filter having a higher attenuation for wavelengths that are longer than a second preselected excitation filter cutoff wavelength than for wavelengths that are shorter than said second preselected excitation filter cutoff wavelength.

* * * * *